United States Patent [19]
Riegel

[11] 3,937,744
[45] Feb. 10, 1976

[54] VINYL CHLORIDE PROCESS

[75] Inventor: Herbert Riegel, Maplewood, N.J.

[73] Assignee: The Lummus Company, Bloomfield, N.J.

[22] Filed: June 15, 1971

[21] Appl. No.: 153,374

Related U.S. Application Data

[63] Continuation-in-part of Ser. No. 831,414, June 9, 1969, abandoned, which is a continuation-in-part of Ser. No. 614,338, Feb. 6, 1967, abandoned.

[52] U.S. Cl............................................. 260/656 R
[51] Int. Cl.² ........................................ C07C 21/02
[58] Field of Search...... 260/656 R, 659 A, DIG. 42

[56] References Cited
UNITED STATES PATENTS

| | | | |
|---|---|---|---|
| 2,407,828 | 9/1946 | Gorin | 260/659 |
| 3,291,846 | 12/1966 | Otsuka et al. | 260/656 |
| 3,501,539 | 3/1970 | Olson et al. | 260/656 |

OTHER PUBLICATIONS
Sundermeyer et al., "Chemische Berichte", Vol. 95 (1962), pp. 1829-1831.

Primary Examiner—James O. Thomas, Jr.
Assistant Examiner—A. Siegel
Attorney, Agent, or Firm—Marn & Jangarathis

[57] ABSTRACT

Process for producing vinyl chloride from ethane by contacting, in a first reactor, ethane and chlorine and/or hydrogen chloride, as fresh feed, and as recycle, hydrogen chloride, ethyl chloride, ethylene and unconverted ethane with a molten mixture, including cuprous chloride, cupric chloride and copper oxychloride, to produce a reaction effluent including vinyl chloride, dichloroethane, primarily 1,2-dichloroethane, and the aforementioned recycle components. The vinyl chloride is recovered as product, the recycle components are recovered and recycled to the first reactor, and the 1,2-dichloroethane is recovered and recycled to the first reactor or contacted in a second reactor with a molten mixture including cuprous and cupric chloride to dehydrochlorinate the 1,2-dichloroethane to vinyl chloride. The molten mixture from the first reactor or second reactor, if employed, is contacted in a third reactor with molecular oxygen to generate copper oxychloride and melt from the third reactor is passed to the first reactor. 1,1-dichloroethane, if produced, may be passed to the first or second reactor for dehydrochlorination to vinyl chloride.

43 Claims, 4 Drawing Figures

INVENTOR.
Herbert Riegel
BY
Marn & Jangarathis

INVENTOR
Herbert Riegel
BY Marn & Jangarathis

VINYL CHLORIDE PROCESS

This application is a continuation-in-part of application Ser. No. 831,414 filed on June 9, 1969, now abandoned, the aforementioned application being a continuation-in-part of application Ser. No. 614,338 filed on Feb. 6, 1967, now abandoned.

This invention relates to the production of vinyl chloride. More particularly, this invention contemplates the production of vinyl chloride using ethane, ethylene or mixtures thereof as starting materials. Still more particularly, this invention utilizes molten salt, which salt serves as catalyst, chlorine transfer medium, oxygen transfer medium, and heat transfer medium. Further, this invention contemplates the recovery, recycle, and ultimate conversion to vinyl chloride product, of unconverted ethane, ethyl chloride and dichloroethane.

Still further, this invention provides for the utilization of hydrogen chloride, both that produced by the process of this invention and that added externally from other operations, and both that in the anhydrous state and that present in aqueous solution as hydrochloric acid.

In the prior art, vinyl chloride is generally produced from ethylene and chlorine feeds. Chlorine is contacted with ethylene at temperatures of from about 100°F. to 300°F., perhaps in the presence of a catalyst to form a 1,2-dichloroethane intermediate. The 1,2-dichloroethane intermediate is then dehydrochlorinated at a temperature of from about 700°F. to 1000°F. to form vinyl chloride and hydrogen chloride.

Commercial feasibility of this method depends on the economic recovery of the hydrogen chloride which is produced. One technique is to react the hydrogen chloride with acetylene to produce vinyl chloride. Alternatively, the hydrogen chloride is used to produce more 1,2-dichloroethane intermediate which is then dehydrochlorinated to produce vinyl chloride. According to this method, ethylene, hydrogen chloride and oxygen are contacted at about 500°F. to 700°F. over a copper chloride-based catalyst in either a fixed bed or fluidized bed reactor. The reaction is exothermic and, consequently, heat must be removed from the reaction apparatus.

Several problems are associated with the conventional 1,2-dichloroethane dehydrochlorination. One problem is that to transfer the required endothermic reaction heat to the 1,2-dichloroethane reactant intube, the tubewall must be substantially hotter than the reaction temperature intube. As a result, some coke and tar formation occurs on the hotter tube which causes additional resistance to heat transfer. This, in turn, necessitates a still higher tubewall temperature. As a consequence, the fouling of the reactor tubes frequently requires termination of operations for the purpose of cleaning the tubes. Another problem relates to the formation of acetylenic and diolefinic by-product compounds in the vinyl chloride. With increasing reaction severity — usually at once-through 1,2-dichloroethane conversions in excess of about 40% to 50% — acetylenic and diolefinic compounds are formed. These compounds adversely affect the polymerization of vinyl chloride and also the quality of the polymer product. Therefore the concentration of the acetylenic and diolefinic contaminants must be limited to less than about 20 ppm in the vinyl chloride monomer. In general, the dehydrochlorination process is operated at about 60% conversion in order to eliminate coking and the production of unwanted by-products.

In accordance with the present invention, an improved process for producing vinyl chloride is provided by the use of melts of multivalent metal chlorides for both the chlorination of ethane and/or ethylene and the dehydrochlorination of dichloroethane (the dichloroethane primarily being 1,2-dichloroethane and also 1,1-dichloroethane).

The use of copper chloride melts for the chlorination of hydrocarbons is known in the art, as exemplified by U.S. Pat. No. 2,407,828 to Gorin; Canadian Pat. No. 711,287 to Bender et al.; and Canadian Pat. No. 705,925 to Bender et al. U.S. Pat. No. 2,498,552 to Kilgren et al. and U.S. Pat. No. 2,498,546 disclose the use of fluidized solid supported copper chloride for the chlorination of hydrocarbons and further indicate that melts may be employed in lieu of the fluidized solids.

Although the hereinabove noted prior art discloses the use of copper chlorides, both as melts and as fluidized solids, for the chlorination of hydrocarbons, such noted prior art does not disclose an overall process specifically directed to the production of vinyl chloride. In addition, such noted prior art does not disclose the use of copper chlorides, either as melts or as fluidized solids, for the dehydrochlorination of dichloroethane.

The primary object of the present invention is to provide an improved and economical method for the production of vinyl chloride.

Another object of the invention is to provide a method whereby vinyl chloride can be produced using either ethylene, ethane, or mixtures thereof.

Another object is to provide a method whereby vinyl chloride can be produced using either chlorine, hydrogen chloride, or mixtures thereof.

A further object is to provide a method for the production of vinyl chloride whereby the chlorine values contained in hydrogen chloride reaction intermediate may be utilized.

A still further object is to provide a highly selective chlorination process for the conversion of ethane and ethylene to vinyl chloride.

A still further object is to provide a method for the production of vinyl chloride wherein ethyl chloride reaction intermediate is converted to vinyl chloride product.

A further object is to provide a method for the production of vinyl chloride wherein dichloroethane reaction intermediate is converted to vinyl chloride product.

Another object is to provide a method for the production of vinyl chloride wherein ethylene reaction intermediate is converted to vinyl chloride product.

A further object is to provide a process for the production of vinyl chloride wherein the hydrogen chloride may be either anhydrous material or hydrochloric acid.

Another object is to provide a reactor system designed to accomplish all of the above objects.

A still further object is to provide a reactor system wherein all the reaction steps necessary to produce vinyl chloride from ethane, ethylene, or combinations of the two, are accomplished within an integrated section.

Still another object is to provide an effective and economical process for producing vinyl chloride from ethane.

These and other objects of the present invention will be obvious by reference to the following description, claims and the attached drawings, wherein:

Figure 1:
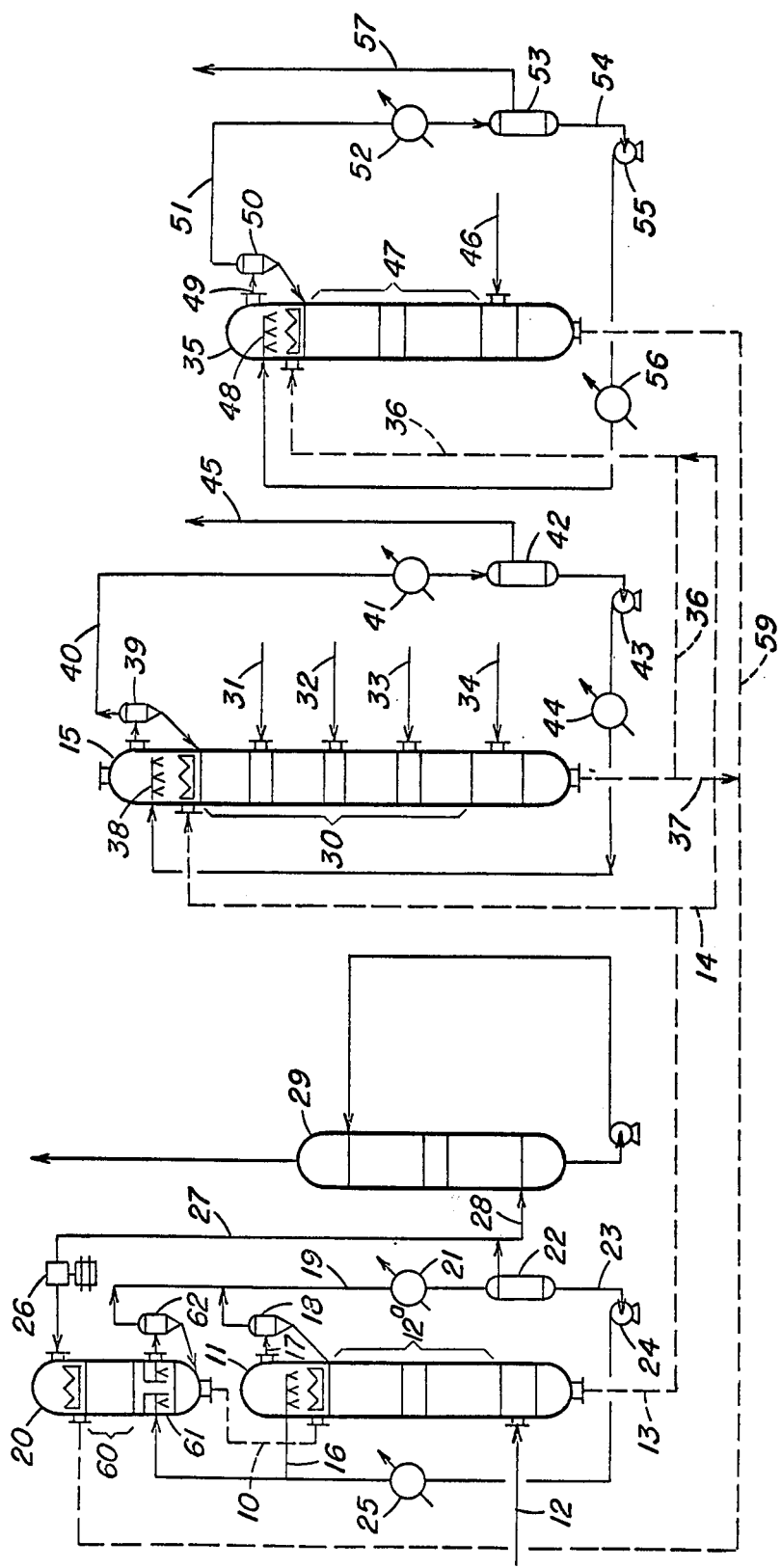
FIG. 1 is a schematic flow diagram of the reaction portion of an embodiment of the process of the invention.

The objects of this invention are broadly accomplished in one aspect by contacting a feed containing ethane and/or ethylene with a melt containing a multivalent metal chloride in both its higher and lower valence state to produce an effluent containing vinyl chloride and dichloroethane. (The dichloroethane reaction product is generally a mixture of 1,2-dichloroethane and 1,1-dichloroethane, primarily 1,2-dichloroethane, and in some cases, the reaction effluent could contain only small amounts of 1,1-dichloroethane whereby the dichloroethane product is essentially 1,2-dichloroethane. As hereinafter employed, dichloroethane generically refers to 1,2-dichloroethane and/or 1,1-dichloroethane) The dichloroethane is separated from the effluent and the dichloroethane is contacted with a melt containing a multivalent metal chloride in both its higher and lower valence state to dehydrochlorinate the dichloroethane to vinyl chloride. The contacting of the multivalent metal chlorides with ethane and/or ethylene and dichloroethane may be effected in the presence of other reagents, as hereinafter described, with reference to preferred embodiments of the invention. Thus, the overall process in its broadest aspect involves production of vinyl chloride and dichloroethane from ethane and/or ethylene by contacting the ethane and/or ethylene with a molten mixture of a multivalent metal chloride in both its higher and lower valence state, hereinafter referred to as "chlorination," although reactions other than chlorination are effected, separation of the dischloroethane from the reaction effluent and production of vinyl chloride from the dichloroethane by contacting the dichloroethane with a molten mixture of a multivalent metal chloride in both its higher and lower valence state hereinafter referred to as "dehydrochlorination." Thus, the chlorination of ethane and/or ethylene and the dehydrochlorination of dichloroethane are both effected in the presence of a molten salt mixture which, as hereinafter described, provides for improved production of vinyl chloride.

The melt contains a chloride of a multivalent metal; i.e., a metal having more than one positive valence state, such as manganese, iron, copper, cobalt, and chromium, preferably copper. In the case of higher melting multivalent metal chlorides, such as copper chlorides, a metal salt melting point depressant which is non-volatile and resistant to the action of oxygen at the process conditions, such as a chloride of a univalent metal, i.e., a metal having only one positive valence state, is added to the multivalent metal chloride to form a molten salt mixture having a reduced melting point. The univalent metal chlorides, are preferably alkali metal chlorides, such as potassium and lithium chloride in particular, but it is to be understood that other metal chlorides and mixtures thereof, such as the heavy metal chlorides, i.e., heavier than copper, of Groups I, II, III and IV of the Periodic Table; e.g., zinc, silver, and thallium chloride, may also be employed. The metal chloride melting point depressant is added in any amount sufficient to maintain the salt mixture as a melt at the reaction temperatures, and is generally added in an amount sufficient to adjust the melting point of the molten salt mixture to a temperature of below about 500°F. In the case of a salt mixture of copper chlorides and potassium chloride, the composition of the melt ranges between about 20% and about 40%, preferably about 30%, by weight, potassium chloride, with the remainder being copper chlorides. It is to be understood, however, that in some cases the catalyst melt may have a melting point higher than 500°F., provided the catalyst remains in the form of the melt throughout the processing steps. It is further to be understood that the melt may contain a mixture of multivalent metal chlorides or other reaction promoters. It is also to be understood that in some cases, metal chloride may be maintained as a melt without the addition of a univalent metal halide.

The reaction sequence for converting ethane and/or ethylene to vinyl chloride in the chlorination zone, using copper chloride as a representative example, is believed to be represented by the following equations:

$$2CuCl_2 \rightarrow 2CuCl + Cl_2 \quad (1)$$
$$C_2H_6 + Cl_2 \rightarrow C_2H_5Cl + HCl \quad (2)$$
$$C_2H_4 + Cl_2 \rightarrow C_2H_4Cl_2 \quad (3)$$
$$C_2H_4Cl_2 \rightarrow C_2H_3Cl + HCl \quad (4)$$
$$C_2H_5Cl \rightarrow C_2H_4 + HCl \quad (5)$$
$$C_2H_5Cl + Cl_2 \rightarrow C_2H_4Cl_2 + HCl \quad (6)$$
$$C_2H_4Cl_2 \rightarrow C_2H_3Cl + HCl \quad (7)$$

It should be apparent from the hereinabove described reaction sequence, as represented by the above equations, that there is a continuous depletion of the higher valent metal chloride; i.e., cupric chloride, and a net production of hydrogen chloride. Therefore, if the process is to be effected on a continuous basis, a provision must be made for regeneration of the cupric chloride and disposal of the hydrogen chloride.

In accordance with the preferred embodiment of the invention, the melt containing the multivalent metal chloride, in both its higher and lower valence state, may be initially contacted in a separate reaction zone with an oxygen-containing gas to produce the oxychloride of the metal, and the melt, now also containing the oxychloride of the multivalent metal, is then contacted in a chlorination zone with chlorine and/or hydrogen chloride and the feed containing ethane and/or ethylene to produce vinyl chloride. The reaction between the melt and the oxygen-containing gas, using copper chloride as a representative multivalent metal chloride, is represented by the following equation:

$$2CuCl + \tfrac{1}{2}O_2 \rightarrow CuO \cdot CuCl_2 \quad (8)$$

The copper oxychloride then reacts with the hydrogen chloride generated during the production of the vinyl chloride as represented by the following equation:

$$CuO \cdot CuCl_2 + 2HCl \rightarrow 2CuCl_2 + H_2O \quad (9)$$

Thus, in accordance with this embodiment, there is no net production of hydrogen chloride and no net depletion of cupric chloride, and in fact, in order to operate the process on a continuous basis, chlorine and/or hydrogen chloride must be added to the system as represented by the following overall equations:

$$C_2H_6 + \tfrac{1}{2}Cl_2 + \tfrac{3}{4}O_2 \rightarrow C_2H_3Cl + 3/2 H_2O \quad (10)$$
$$C_2H_6 + HCl + O_2 \rightarrow C_2H_3Cl + 2H_2O \quad (11)$$
$$C_2H_4 + \tfrac{1}{2}Cl_2 + \tfrac{1}{4}O_2 \rightarrow C_2H_3Cl + \tfrac{1}{2}H_2O \quad (12)$$
$$C_2H_4 + HCl + \tfrac{1}{2}O_2 \rightarrow C_2H_3Cl + H_2O \quad (13)$$

It is to be understood that hydrogen chloride may be added to the system by the introduction of a partially chlorinated hydrocarbon to generate hydrogen chloride in situ, since partially chlorinated hydrocarbons generate hydrogen chloride as represented by hereinabove equations (5) and (7). The hydrogen chloride and/or chlorine may be added to the system either with the oxygencontaining gas or in the chlorination zone with the ethane and/or ethylene feed, preferably with the ethane and/or ethylene feed so as to eliminate the necessity of providing means for recovering hydrogen chloride and/or chlorine from the gaseous effluent from the oxygen-contacting step. In addition, the addition of chlorine and/or hydrogen chloride with the ethane and/or ethylene feed improves the yield of vinyl chloride.

In accordance with another embodiment of the invention, the oxygen-containing gas may be introduced into the chlorination zone with the ethane and/or ethylene feed to produce the oxychloride of the multivalent metal, in situ, but such a procedure is not preferred in that there may be a loss of ethane and/or ethylene feed by combustion. In addition, the quantities of oxygen and ethane and/or ethylene would have to be regulated to prevent explosive compositions.

In accordance with a further embodiment of the invention, the higher valent metal chloride may be regenerated by contacting the melt with a chlorine-containing gas, such contacting being effected either simultaneously with the production of vinyl chloride from the ethane and/or ethylene feed or in a separate reaction zone. The regeneration of the higher valent multivalent metal chloride, using copper chloride as a representative example, may be represented by the following equation:

$$2CuCl + Cl_2 \rightarrow 2CuCl_2 \quad (14)$$

and the overall reaction, using ethylene as a representative feed, by the following equation:

$$C_2H_4 + Cl_2 \rightarrow C_2H_3Cl + HCl \quad (15)$$

This procedure is not particularly preferred in that there is a net production of hydrogen chloride.

In accordance with still another embodiment of the invention, the hydrogen chloride generated during the production of vinyl chloride in the chlorination zone may be recovered from the reaction effluent, and employed in a separate reaction zone, along with an oxygen-containing gas, to regenerate the higher valent metal chloride, as represented by the following equation:

$$2HCl + 2CuCl + \tfrac{1}{2}O_2 \rightarrow 2CuCl_2 + H_2O \quad (16)$$

This procedure is also less preferred in that provision must be made for recovering the hydrogen chloride from the chlorination zone reaction effluent.

Although several embodiments for the chlorination of ethane and/or ethylene by the use of melts containing a multivalent metal chloride in both its higher and lower valence state have been described, the preferred embodiment for such chlorination involves contacting of the melt with molecular oxygen in a first reaction zone to provide a molten salt mixture which further includes the oxychloride of the multivalent metal, followed by circulating the melt from the first reaction zone to a second reaction zone (chlorination zone) wherein the melt is contacted with ethane and/or ethylene and chlorine and/or hydrogen chloride to produce a chlorinated effluent, including vinyl chloride. This embodiment is preferred in that significantly higher yields of vinyl chloride are obtained by effecting the chlorination with the direct addition of chlorine and/or hydrogen chloride into the chlorination reactor.

The dichloroethane (primarily 1,2-dichloroethane) produced along with the vinyl chloride in the chlorination zone, as hereinabove described with respect to several embodiments of the invention, is recovered from the chlorination zone reaction effluent, and dehydrochlorinated to vinyl chloride by contacting the dichloroethane with a melt containing a multivalent metal chloride in both its higher and lower valence state, with the reaction being represented by the hereinabove equation (7):

$$C_2H_4Cl_2 \rightarrow C_2H_3Cl + HCl \quad (7)$$

The melt may also contain the oxychloride of the multivalent metal whereby there is essentially no net production of hydrogen chloride, as represented by hereinabove equation (9):

$$2HCl + CuO \cdot CuCl_2 \rightarrow 2CuCl_2 + H_2O \quad (9)$$

The use of the hereinabove described melts for the dehydrochlorination of dichloroethane (in particular the 1,2-dichloroethane) to vinyl chloride is particularly advantageous in that the melts direct the dehydrochlorination to the production of vinyl chloride at high rates of conversion and high vinyl chloride selectivity. In addition, the reaction effluent is essentially free of diolefinic contaminants which are generally found in the reaction effluents from prior art dehydrochlorination reactions. In accordance with the present invention, the 1,2-dichloroethane, which constitutes the major portion of the dichloroethane produced (in some cases essentially all of the dichloroethane product is 1,2-dichloroethane), may be converted to vinyl chloride at conversion rates greater than 90% while retaining vinyl chloride selectivity at greater than 90%, whereas the prior art processes, in order to convert 1,2-dichloroethane to vinyl chloride at high selectivity, operated at conversion rates of 60%, thereby increasing operating costs. It is to be understood, however, that although the dehydrochlorination of the present invention may be effectively operated at conversions greater than 90%, for some operations, lower conversion rates may be employed.

The chlorination and dehydrochlorination are generally operated at temperatures from about 700° to about 1200°F., preferably from about 750°F. to about 1000°F., although the temperatures may be as low as 575°F., and at pressures from about 1 to about 20 atmospheres. The contacting of the feed and melt is generally effected in a countercurrent fashion, preferably with the feed as a continuous vapor phase, at residence times from about 1 to about 60 seconds although longer residence times may be employed. In the embodiments of the invention wherein the melt is previously contacted with oxygen, in a separate reaction zone, such contacting is generally effected at temperatures from about 600°F. to about 900°F., although higher temperatures may be employed. The preferred operating temperatures for the oxidation of the melt are from about 750°F. to about 870°F.

It should be apparent from the hereinabove noted reaction sequences, that the melt containing the multivalent metal chloride, in some cases, participates in the reaction sequence and accordingly does not behave only as a catalyst. Thus, for example, in the preferred embodiments of the invention, the melt functions to transfer oxygen, and as should be apparent from the hereinabove noted equations, sufficient oxychloride must be produced to provide the oxygen requirements for the reactions, such requirements being greater for ethane as compared to ethylene and greater for hydrogen chloride as compared to chlorine. In general, the oxychloride content of the molten mixture introduced into the chlorination reactor ranges from about 0.5% to about 5.5%, and preferably from about 1% to about 3%, all by weight, of the melt.

The melt, in addition to functioning as a reactant and/or catalyst is a temperature regulator. Thus, the circulating melt has a high heat absorption capacity, thereby preventing runaway reaction during the exothermic chlorination and oxygen-contacting steps. The absorbed heat of reaction may be employed to both heat the various reactants to reaction temperature and supply heat for the endothermic dehydrochlorination. It should be apparent, however, that if additional heating or cooling is required such heating or cooling may be supplied from an external source. It should also be apparent that the heat absorption capacity of the melt functions to limit temperature variations, i.e., temperature gradients, during the reactions.

Thus, as should be apparent from the hereinabove description of the present invention, vinyl chloride may be produced from ethane and/or ethylene by contacting thereof with a melt containing a multivalent metal chloride in both its higher and lower valence state, in the absence or presence of chlorine and/or hydrogen chloride, and in the absence or presence of the corresponding oxychloride, preferably in the presence of chlorine and/or hydrogen chloride and in the presence of the oxychloride, followed by contacting or recovered dichloroethane with a melt containing a multivalent metal chloride in both its higher and lower valence state to dehydrochlorinate the dichloroethane to vinyl chloride. The chlorination and dehydrochlorination, as hereinafter described, are preferably effected by using the same circulating melt, but it should be readily apparent that each of the two steps could be effected with molten mixtures having different multivalent metal chlorides. Similarly, melts of identical compositions could be employed in each of the steps, without circulating such identical melts between the two steps.

In accordance with a preferred embodiment of the invention, vinyl chloride is produced from a net feed of ethane, molecular oxygen and chlorine and/or hydrogen chloride, using copper chlorides as the molten salt mixture, with the intermediate products produced during the reaction being effectively converted to vinyl chloride.

The molten salt mixture, preferably containing from about 20% to about 40% potassium chloride, as a melting point depressant, with the remainder being copper chlorides, all by weight, is contacted in a first reaction zone with molecular oxygen to produce copper oxychloride. The cupric chloride content of the melt is generally at least about 16%, by weight, of the melt, and generally from about 18% to about 50%, by weight, in order to provide sufficient cupric chloride for the subsequent chlorination and dehydrochlorination reactions. It is to be understood however that lower amounts of cupric chloride may also be employed by increasing salt circulation rates and residence times. As a result of the various reactions which occur during the chlorination and dehydrochlorination steps, the cupric chloride content of the melt does not significantly vary through the various reaction zones. The molecular oxygen is preferably introduced in an amount, and at a rate, to provide a molten salt mixture containing from about 0.5% to about 5.5%, preferably from about 1% to about 3%, all by weight, of copper oxychloride. It is to be understood that minor amounts of chlorine and/or hydrogen chloride could also be introduced into the first reaction zone, but in accordance with this preferred embodiment, the major portion of the chlorine and/or hydrogen chloride is added to the chlorination zone.

The molten salt mixture, now containing copper oxychloride, is circulated to a second reaction zone (chlorination zone) wherein the molten salt is contacted with ethane and chlorine and/or hydrogen chloride as fresh feed, in addition to recycle unconverted ethane, and recycle ethyl chloride and ethylene generated as reaction intermediates. The recycle, as hereinafter described may also include hydrogen chloride and 1,2-dichloroethane and/or 1,1-dichloroethane. The chlorine, if used, is added in amounts which approximate stoichiometric quantities in order to eliminate the presence of chlorine in the reaction effluent, thereby also eliminating the necessity for chlorine recovery and recycle. The reactions which occur in the chlorination zone are believed to be best represented by hereinabove equations (1) – (7) and (9). Thus, fresh ethane and chlorine and/or hydrogen chloride feed are converted to ethyl chloride, ethylene, dichloroethane (both 1,1-dichloroethane and 1,2-dichloroethane, primarily 1,2-dichloroethane) and vinyl chloride, with the recycle ethyl chloride and ethylene also being ultimately converted to vinyl chloride. The hydrogen chloride generated, in situ, reacts with the copper oxychloride of the melt to produce cupric chloride. In some cases, 100% conversion of the generated hydrogen chloride is not achieved and, accordingly, the reaction effluent may also include some hydrogen chloride. The chlorination reaction effluent withdrawn from the chlorination zone includes, in addition to unconverted ethane, ethylene, ethyl chloride, dichloroethane, hydrogen chloride (if any), water vapor and vinyl chloride. The chlorination reaction effluent further includes minor portions of one or more of the following: dichloroethylenes, trichloroethylene, tetrachloroethylene, trichloroethanes, and tetrachloroethane.

The chlorination reaction effluent is passed to a separation and recovery zone wherein vinyl chloride is recovered as reaction product, ethyl chloride, ethylene and ethane are recovered as recycle streams to the chlorination zone and 1,2-dichloroethane is recovered for recycle to either the chlorination zone or a dehydrochlorination zone. In general, the recycle weight ratio of ethyl chloride to fresh ethane feed ranges from about 0.3:1 to about 14:1 and the recycle weight ratio of ethylene to fresh ethane feed ranges from about 0.03:1 to about 1.2:1.

If a separate dehydrochlorination zone is employed, the 1,2-dichloroethane produced in the chlorination zone is introduced into the dehydrochlorination zone and contacted therein with the molten salt from either the first reaction zone, the second reaction zone (chlorination zone), or molten salt from both zones, to effect dehydrochlorination of the 1,2-dichloroethane to vinyl chloride. The reaction effluent includes vinyl chloride and any unconverted 1,2-dichloroethane. In addition, if the melt employed in the dehydrochlorination zone is obtained from the second reaction zone, the dehydrochlorination reaction effluent includes hydrogen chloride, and if the melt is obtained from the first reaction zone, the effluent includes water vapor and any hydrogen chloride which does not react with the copper oxychloride present in the melt. The dehydrochlorination reaction effluent is introduced into a separation and recovery zone to recover the various components, with vinyl chloride being recovered as reaction product, hydrogen chloride, if any, being recycled to the chlorination zone, and unconverted 1,2-dichloroethane being recycled to the dehydrochlorination zone. It is also to be understood that in some cases, one or more of the other components in the chlorination effluent; i.e., ethyl chloride, ethylene and ethane, may be introduced into the separate dehydrochlorination reaction zone, if employed, instead of into the chlorination reaction zone.

As hereinabove noted, the chlorination reaction effluent may also include 1,1-dichloroethane, and the 1,1-dichloroethane may be recovered with the 1,2-dichloroethane and dehydrochlorinated in the dehydrochlorination zone. In some cases, it may be desirable to separately recover 1,1-dichloroethane and 1,2-dichloroethane to provide essentially only a 1,2-dichloroethane feed to the dehydrochlorination zone (by separately recovering 1,1- and 1,2-dichloroethane the chlorinated components, in particular dichloroethylenes, which boil between the isomers of dichloroethane may also be eliminated from the feed to the dehydrochlorination zone), and in such cases, the 1,1-dichloroethane may be recovered separately from the 1,2-dichloroethane and recycled to the chlorination zone wherein the 1,1-dichloroethane contacts the molten salt and is dehydrochlorinated to vinyl chloride. Accordingly, in accordance with the preferred embodiment, 1,2-dichloroethane reaction intermediate is dehydrochlorinated to vinyl chloride either in the chlorination zone or in a separate dehydrochlorination reaction zone, either in the presence or absence of 1,1-dichloroethane, and the 1,1-dichloroethane reaction intermediate, if present, is dehydrochlorinated to vinyl chloride either in the separate dehydrochlorination reaction zone or in the chlorination zone.

The molten salt to feed weight ratio (based on total feed to the chlorination reaction zone) is preferably from about 25:1 to about 200:1, with the molten salt, at such high salt circulation rates, acting as a heat sink, whereby there is little temperature variation between the various zones; i.e., in general the temperature fluctuation between the various zones is no greater than about 130°F. and generally from about 15°F. to about 50°F.

It should be readily apparent that in accordance with the preferred embodiment, vinyl chloride is effectively produced from ethane, chlorine and/or hydrogen chloride and oxygen as a result of the recycle of essentially all reaction intermediates, with the overall reaction being represented by equations (10) and/or (11).

It is also to be understood that, as hereinabove noted, other chlorinated hydrocarbons, such as, dichloroethylenes, trichloroethylene, tetrachloroethylene, trichloroethanes, tetrachloroethane, carbon tetrachloride and the like, may be produced during the various reactions. In some cases, some of these other chlorinated hydrocarbons are present in the various recycle streams in that complete separation of such other chlorinated hydrocarbons is not possible.

It is also to be understood that the preferred ethane feed could also contain some ethylene, and/or propane and/or methane as for example, in the case where a $C_2$ stream is recovered from a refinery.

The invention will now be further described with reference to embodiments thereof illustrated in the accompanying drawings. It is to be understood however, that the scope of the invention is not to be limited thereby. It is further to be understood that the molten copper chloride salts are highly corrosive and, accordingly, the processing equipment must be suitably protected; e.g., the reactors may be lined with ceramic. Similarly, if pumps are used for transporting the molten salts they must also be protected. The molten salts, however, are preferably transferred between the reactors by the use of gas lifts, as known in the art.

Referring now to FIG. 1, a molten chloride salt, such as a mixture of potassium chloride, cupric and cuprous chloride, in line 10, at a temperature of from 600°F. to 900°F. is introduced into the top of an oxidation vessel 11 maintained at a pressure of from about 1 to about 20 atmospheres. A compressed oxygen-containing gas, such as air, in line 12 is introduced into the bottom of vessel 11 and is passed in countercurrent contact to the descending molten salt. The vessel 11 may be provided with one or more sections of packing, generally indicated as 12a, to produce intimate and effective contact between the compressed gas and molten salt. The molten salt is oxidized to produce oxychloride, with the concurrent evolution of heat. The residence time of the molten salt within the vessel 11 is from about 1 to about 60 seconds.

The effluent gas leaving the packing near the top of vessel 11 is at a temperature of from about 600°F. to 900°F., and is contacted with a spray of suitable quench liquid, for example, from one of the processing streams, in line 16 having a temperature of about 100°F. A suitable quench liquid would be water having dissolved hydrogen chloride. The gas is cooled by such contact with the result that vaporized and entrained salts are condensed and eliminated from the gas stream. The quench liquid spray is concurrently vaporized and, together with the effluent gas, is withdrawn from the top of vessel 11. The total gaseous effluent is passed through line 17 to a cyclone separator 18 for the elimination of any solid material which is returned to the vessel 11. The gaseous effluent is thereafter combined with another gaseous effluent in line 19 as more fully hereinafter described. The combined gaseous effluent is cooled to about 100°F. to 150°F. in heat exchanger 21 to condense out the vaporized quench liquid. The condensed quench liquid is separated from the remaining gaseous effluent in vapor/liquid separator 22. The quench liquid is passed through line 23 by pump 24 to heat exchanger 25 to cool the quench liquid to a temperature of about 100°F., with a portion being returned to the upper portion of vessel 11. The gaseous effluent in separator 22 is divided with a portion being passed through line 28 into a caustic scrubber 29. From scrubber 29, inert gases, such as nitrogen introduced with the oxygen in the oxygen-containing feed gas are readily discharged from the reactor system.

The molten salt, now containing the copper oxychloride, at a temperature of from about 700°F. to 1200°F. is withdrawn from the bottom of vessel 11 through line 13 and passed to the top of a reactor 15. Alternatively, a portion of the molten salt in line 13 may be passed through line 14 for introduction into a dehydrochlorination reactor, as hereinafter described. The reactor 15 is operated at a temperature of from about 700°F. to about 1200°F., at a pressure of from 1 to 20 atmospheres, and a residence time of 1 to 60 seconds. The reactor 15 is provided with sections of packing, generally indicated as 30, designed to effect intimate and effective contact between the gaseous feed components and the molten salt as more fully hereinafter described. Fresh feed hydrogen chloride, if any, and recycle ethyl chloride, as more fully hereinafter described, at a suitable temperature; e.g., from 100°F. to 200°F., or up to 800°F. are introduced into the upper portion of reactor 15 through line 31. Combined recycle components ethane, ethylene and hydrogen chloride at a suitable temperature; e.g., from 100°F. to 200°F. or up to 800°F. are introduced into reactor 15 through line 32 at a point below line 31. The introduction into reactor 15 of the recycle streams and the fresh hydrogen chloride stream (if any) may be further divided, reversed in position, or may be combined into one stream.

Fresh chlorine is introduced into reactor 15 through line 33 at a point below the recycle feed positions 31 and 32. Fresh feed ethane, ethylene, or mixtures thereof, preferably ethane fresh feed, is introduced through line 34 into reactor 15 near the lower portion thereof. The hydrocarbon fresh feed in line 34 should be introduced at or near the bottom of the reactor 15.

It is also to be understood that both recycle and fresh feed may be introduced at a single point at the bottom of the reactor.

The gaseous effluent at the top of the upper packed section in reactor vessel 15 is at a temperature between 700°F. and 1200°F., and is cooled by a spray of suitable quench liquid obtained, for example, from one of the processing streams, in line 38 to about 300°F. A suitable quench liquid would be one or more of the chlorinated hydrocarbons produced in reactor 15. Such temperature is above the dew point temperature of the combined gaseous reaction effluent and vaporized quench liquid. The total gaseous effluent is passed into cyclone separator 39 to remove any solids and is then passed through line 40 to condenser 41 to condense the quench liquid. The mixed vapor/liquid stream is introduced into separator 42 with the condensed quench liquid being passed by pump 43 to cooler 44 wherein the liquid is cooled to about 150°F. The cooled quench liquid is then passed to spray device 38 in reactor 15. The gaseous effluent from separator 42 at about 230°F. is passed through line 45 to a separation section illustrated in FIG. 2 as more fully hereinafter described.

The molten salt withdrawn from the bottom of reactor 15 is at a temperature of from about 700°F. to 1200°F., and is passed through line 36 to the top of dehydrochlorination reactor 35 along with any melt in line 14. Alternatively, all or a portion of the melt from the reactor 15 may be passed through line 37 for return to vessel 11 as hereinafter described. Dichloroethane separated in said separation section, is introduced through line 46 at a suitable temperature, e.g., 100° –800°F., into the bottom of the dehydrochlorination reactor 35. Dehydrochlorination reactor 35 includes one or more packed sections, generally indicated as 47, to effect intimate and effective contact between the dichloroethane and molten salt. The dichloroethane is passed in countercurrent contact with the melt to effect the endothermic dehydrochlorination of the dichloroethane to yield vinyl chloride and hydrogen chloride. The reaction is conducted at a temperature of from about 700°F. to about 1200°F., a pressure of about 1 to about 20 atmospheres, with a residence time of about 1 to about 60 seconds. It will be understood that the dichloroethane may also flow cocurrently downwardly with the molten salt.

The gaseous effluent leaving the top of the upper packed section of dehydrochlorination reactor 35 at a temperature of from 700°F. to 1200°F. is cooled by means of a spray of a suitable quench liquid obtained, for example, from one of the processing streams through spray device 48 to lower the temperature of the gaseous effluent and the now vaporized quench liquid to between 300°F. and 400°F. thereby eliminating entrained and vaporized salts. A suitable quench liquid would be one or more chlorinated hydrocarbons recovered from the dehydrochlorination effluent. The total gaseous effluent is withdrawn from the upper part of the reactor 35 through line 49 and is passed into cyclone separator 50 where any solids are removed. The gaseous effluent from separator 50 is passed through line 51 into condenser 52 where, at a temperature of about 150°F. to 200°F., the quench liquid is condensed. The mixed vapor/liquid stream is thereafter passed into separator 53, from which the condensed quench liquid is passed through line 54 by pump 55 to cooler heat exchanger 56 wherein the temperature of the quench liquid is lowered to about 80°F. to 120°F. The cooled quench liquid is then passed to spray device 48 in the top of reactor 35. The effluent vapor at 150° to 200°F. withdrawn from separator vessel 53 is passed through line 57 to the separation section, as more fully hereinafter described. The molten salt at the bottom of the reactor 35, which is at a temperature lower than at the inlet to said reactor 35, is withdrawn through line 59 combined with any molten salt in line 37 and passed to the top of direct heat exchange vessel 20.

Heat exchange vessel 20 comprises one or more packed sections, generally indicated as 60. A portion of the gas withdrawn from separator 22 through line 27, is compressed in compressor 26, and introduced into the top of heat exchange vessel 20 wherein the compressed gas is passed in direct heat exchange contact with the molten salt introduced through line 59. The gas and the molten salt are concurrently passed over the packed sections 60 and are disengaged in the bottom of the heat exchange vessel 20. The gas is cooled by a spray of quench liquid through spray device 61 to eliminate any vaporized or entrained halide salt. A gaseous effluent comprised of the gas introduced through line 27 and now vaporized quench liquid is withdrawn from vessel 20 and passed into cyclone separator 62. In separator 62 any solids are removed from the gaseous effluent. The gaseous effluent withdrawn from separator 62 is passed through line 19 and combined with the gaseous effluent from oxidation vessel 11. The combined gaseous effluent is passed through condenser 21 to condense the quench liquid. The principal purpose of the heat exchange vessel 20 is to bring the molten salt in line 59 to a constant and desired temperature prior to introducing the molten salt into the top of oxidation vessel 11. In general, the overall reaction provides a net exotherm and, therefore, some cooling of the melt in vessel 20 is required.

Figure 2:
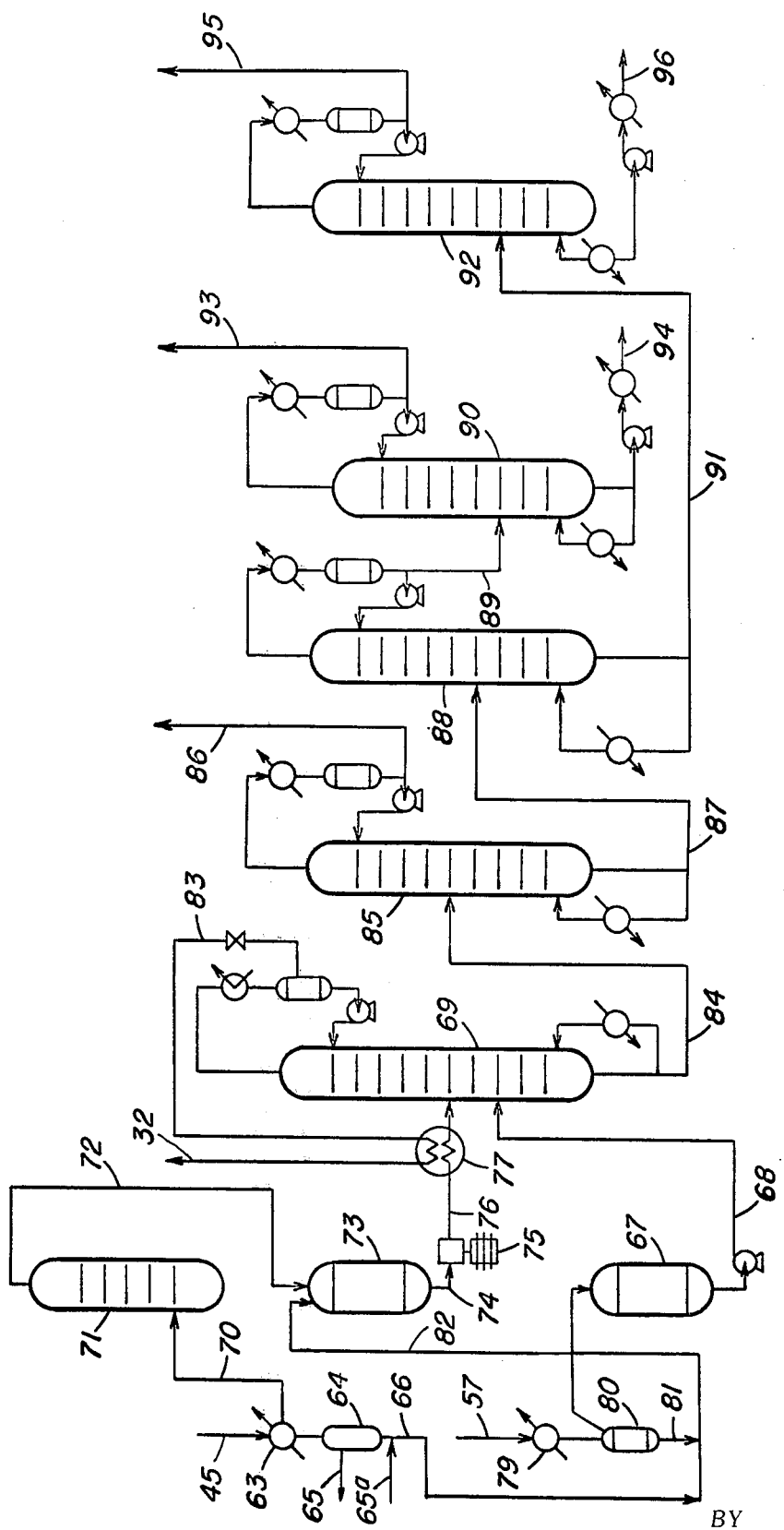
FIG. 2 is a schematic flow diagram of the recovery portion of an embodiment of the process of the invention.

Referring now to FIG. 2, the reactor effluent from reactor 15 in line 45 is comprised of vinyl chloride, hydrogen chloride (if any), dichloroethane, ethyl chloride, water and heavier chlorinated hydrocarbons. The reactor effluent is cooled to about 80° to 100°F. in condenser 63 primarily to condense water and heavier chlorinated hydrocarbons. The condensed water and heavier chlorinated hydrocarbons are introduced into a separator 64 to separate the water from the heavier chlorinated hydrocarbons. The water phase withdrawn from separator 64 through line 65 is neutralized and stripped of entrained and dissolved chlorinated hydrocarbon in a stripping column (not shown). The separated chlorinated hydrocarbons (from the stripping column) in line 65a are combined in line 66 with the heavier chlorinated hydrocarbons withdrawn from vessel 64 for subsequent processing.

The remaining portion of the reactor effluent gaseous stream, after cooling in condenser 63, is passed through line 70 into an column 71 wherein acid gases, principally any carbon dioxide present, are removed by any of several well-known acid gas absorption or adsorption systems. A gaseous effluent is withdrawn from column 71 through line 72 and is passed into dryer 73 for removal of residual water.

The effluent vapor in line 57 from dehydrochlorination reactor 35 is passed through a condenser 79 wherein the effluent vapor is cooled to about 80° to about 120°F. primarily to condense unconverted dichloroethane which is passed to vessel 80. The unconverted dichloroethane withdrawn from condenser 80 through line 81 is combined with chlorinated hydrocarbons in line 66. The combined stream is passed through dryer 67 and is introduced through line 68 into distillation column 69. The uncondensed gaseous effluent from condenser 79 is withdrawn through line 82 and is passed into dryer 73 wherein the uncondensed gaseous effluent is combined with gaseous effluent in line 72. The dried gas withdrawn from dryer 73 through line 74 is passed to compressor 75 and compressed to about 10 to about 30 atmospheres. The compressed gas is thereafter passed through line 76 through heat exchanger 77 and is introduced into distillation column 69.

Distillation column 69 is operated at temperatures and pressures to produce a gaseous overhead comprised of ethane, ethylene and hydrogen chloride. The gaseous overhead in line 83 is passed through heat exchanger 77 and is introduced into reactor vessel 15, through line 32, as shown in FIG. 1. The column bottoms consisting of chlorinated hydrocarbons is passed through line 84 to a distillation column 85. It is to be understood that if the molten mixture employed in dehydrochlorination reactor 35 contains oxychloride, the overhead from column 69 does not include hydrogen chloride.

Distillation column 85 is operated at temperatures and pressures to form an overhead primarily comprised of vinyl chloride with minor amounts of impurities. The overhead in line 86 is passed, if necessary, to a purification system (not shown) to produce monomer grade vinyl chloride. The column bottoms from distillation column 85 is passed through line 87 to a distillation column 88.

Distillation column 88 is operated at temperatures and pressures to produce an overhead stream comprising all remaining chlorinated hydrocarbons boiling below dichloroethane (both 1,2- and 1,1-dichloroethane). The overhead stream from column 88 is passed through line 89 into distillation column 90. The bottoms product from distillation column 88 containing dichloroethane and higher boiling chlorinated products is passed through line 91 into a distillation column 92.

Distillation column 90 is operated at pressures and temperatures designed to form an overhead stream substantially comprised of pure ethyl chloride which is passed through lines 93 and 31 to the reactor 15, as shown in FIG. 1. The bottoms from distillation column 90 consisting largely of dichloroethylenes is withdrawn from the system through line 94.

Distillation column 92 is operated at such temperatures and pressures designed to produce an overhead comprised substantially of pure dichloroethane (primarily 1,2-dichloroethane and also 1,1-dichloroethane). It is to be understood, however, that the overhead stream may also contain some dichloroethylenes, trichloroethylene and carbon tetrachloride. The overhead stream is passed through lines 95 and 46 to the dehydrochlorination reactor 35, as shown in FIG. 1. The bottoms stream from distillation column 92 consisting primarily of one or more of the following: trichloroethylene, trichloroethane, perchloroethylene and tetrachloroethane, is withdrawn from the system, through line 96.

The hereinabove described embodiment may be modified within the spirit and scope of the invention. Thus, for example, although the embodiment has been particularly described with respect to the use of ethane as the fresh hydrocarbon feed, with ethylene as recycle, the fresh feed could be ethylene or a mixture of ethylene and ethane. Similarly, although the embodiment has been particularly described with the use of chlorine as the fresh chlorinating agent, hydrogen chloride or a mixture of hydrogen chloride and chlorine could be employed.

Similarly, the chlorine may be added to the feed other than as described. Thus, for example, hydrogen chloride and/or chlorine may be introduced into reactor 11 instead of reactor 15. Alternatively, chlorine may be introduced into reactor 11 instead of oxygen, in which case, as hereinabove described, there will be a net production of hydrogen chloride. As a further modification, all or a portion of the oxygen-containing gas may be introduced into reactor 15 instead of reactor 11. It is to be understood, however, that these other methods of adding chlorine to the feed are less preferred as a result of lower yields and/or more costly recovery and recycle.

As another modification, the temperature of the circulating molten mixture may be regulated by controlling the temperature of the lift gas, in which case the heat exchange vessel 20 would be eliminated.

As yet a further modification, the separation and recovery of the various components could be effected in a manner other than as described. This, for example, as hereinabove noted, the presence of 1,1-dichloroethane in the feed to the dehydrochlorinator may not be desirable and in such a case, if 1,1-dichloroethane is present in the chlorination effluent, column 88 is operated to produce an overhead stream comprising all remaining chlorinated hydrocarbons boiling below 1,2-dichloroethane, whereby the 1,1-dichloroethane is taken overhead with the ethyl chloride. Column 90 is then operated to recover, as overhead, ethyl chloride and 1,1-dichloroethane, the aforesaid overhead being recycled to the chlorinator 15.

As a further alternative, column 92 may be omitted, and the bottoms from column 88 (containing 1,2-dichloroethane and heavier components, or 1,1- and 1,2-dichloroethane and heavier components) fed directly to the dehydrochlorination reactor 35. In such an alternative embodiment, a further column would be provided for separating from the dehydrochlorination reaction effluent, those heavier components previously recovered as bottoms in column 92. The further column, however, could be of a smaller capacity than that required for column 92.

As still another alternative, the components of the reaction effluents from the chlorination reactor and the dehydrochlorination reactor may be recovered in separate separation and recovery zones.

It is also to be understood that in the event that there is a separate market for any of the reaction intermediates, one or more of such reaction intermediates may be separately recovered and marketed instead of being recycled.

As still another modification, the chlorination reaction zone and dehydrochlorination reaction zone may be in a single reactor divided into the aforesaid two reaction zones, with the two zones being provided with molten salt from the oxidation reactor; i.e., the molten salt in both reactors includes cuprous chloride, cupric chloride and copper oxychloride, with the molten mixture which is withdrawn from the two zones being passed to the oxidation reaction zone.

As yet a further alternative, one or more of the components recycled to the chlorination reaction zone, i.e., ethyl chloride, ethane and ethylene may be recycled to the dehydrochlorination reaction zone with the dichloroethane, instead of being recycled to the chlorination reaction zone. Thus, for example, unconverted ethane, ethylene and ethyl chloride recovered from the chlorination effluent could be introduced into a separate dehydrochlorination reaction zone or in a separate section of the chlorination reactor along with dichloroethane for ultimate conversion to vinyl chloride. The molten salt to the dehydrochlorination reaction zone would preferably include oxychloride, whereby the effluent would contain little, if any, hydrogen chloride.

Figure 3:
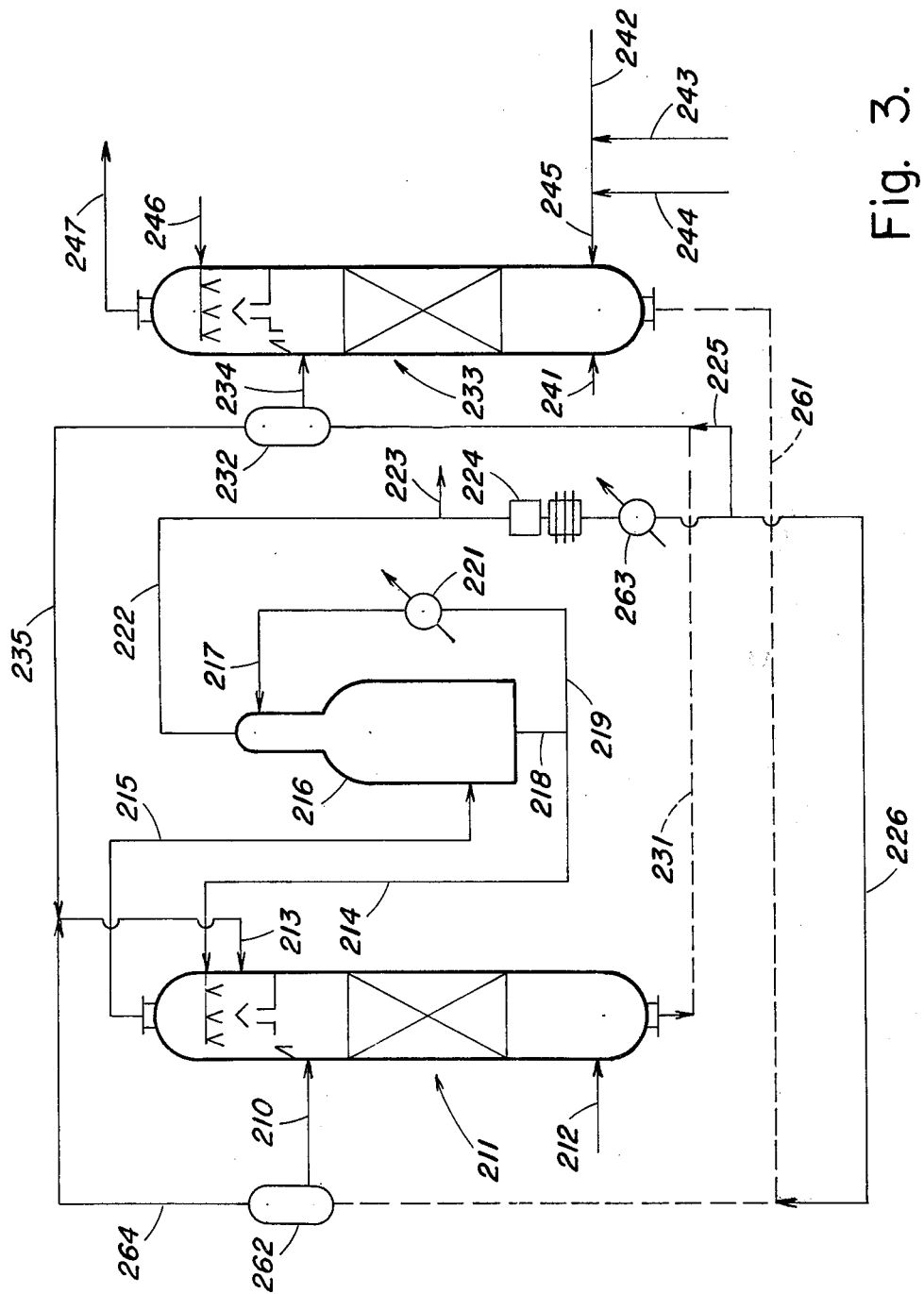
FIG. 3 is a schematic flow diagram of the reaction section of an alternative embodiment of the invention.
Figure 4:
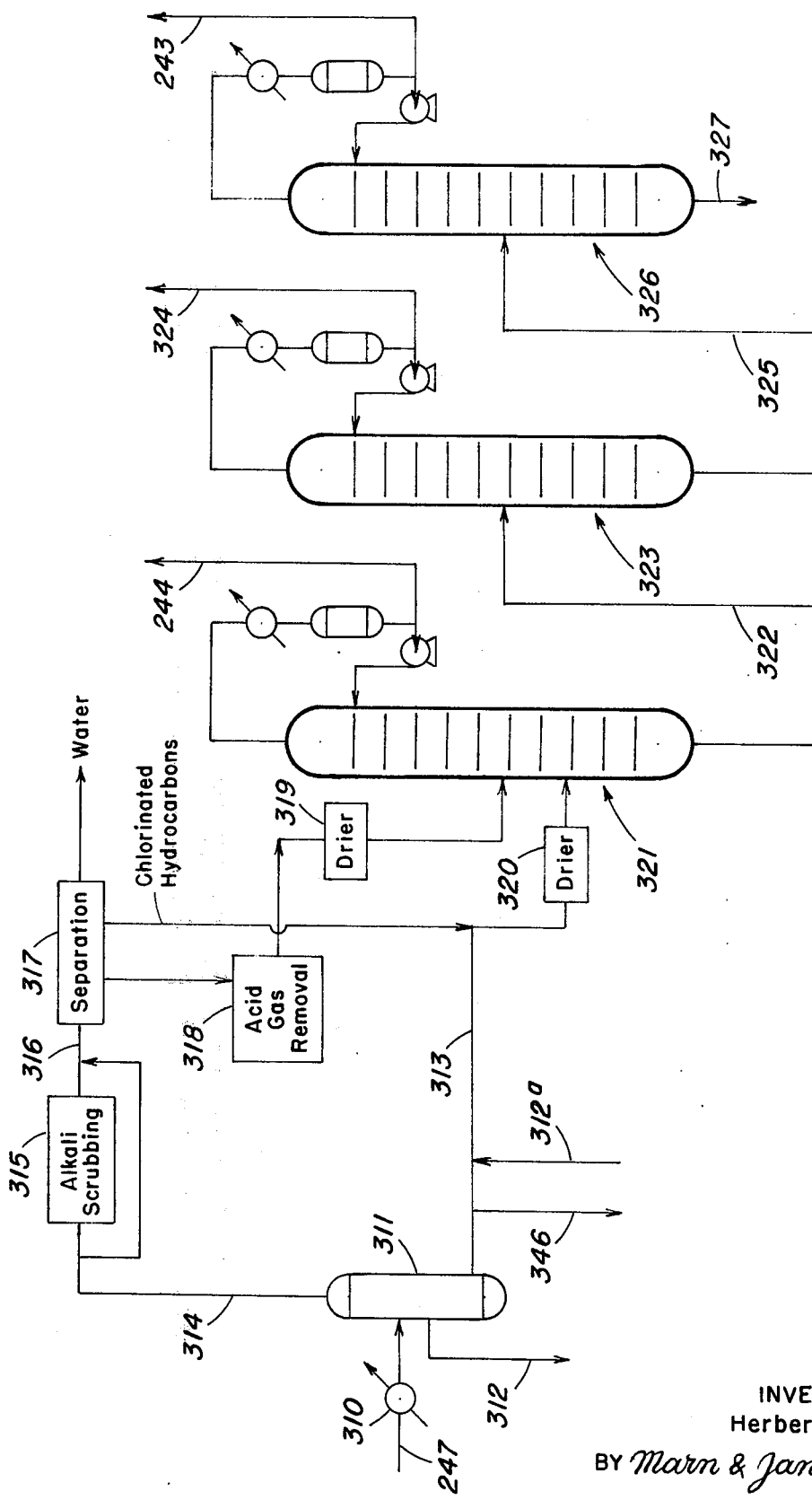
FIG. 4 is a schematic flow diagram of the recovery portion of the alternative embodiment of the process of the invention.

As a further alternative embodiment of the invention, the dichloroethane reaction intermediate, 1,2- and/or 1,1-dichloroethane may be dehydrochlorinated to vinyl chloride in the chlorination vessel and such an alternative embodiment is illustrated in FIGS. 3 and 4 of the drawings. The alternative embodiment of FIGS. 3 and 4 is particularly described with reference to the use of a lift gas for transporting the salt, direct contact quench cooling and the use of the lift gas for adjusting the temperature of the molten salt instead of a separate direct contact heat exchange vessel, which as hereinabove noted are equally applicable to the embodiment of FIGS. 1 and 2.

Referring now to FIG. 3, a molten chloride salt, such as a mixture of potassium chloride, cuprous chloride and cupric chloride in line 210 is introduced into the top of the reaction portion of an oxidation vessel 211 maintained, as hereinabove described, at temperatures and pressures suitable for oxidizing the molten salt. A compressed oxygen-containing gas, such as air, in line 212 is introduced into the bottom of vessel 211 and is passed in countercurrent contact to the descending molten salt, resulting in oxidation of the salt to produce copper oxychloride with the concurrent evolution of heat.

An effluent gas, comprised essentially of the nitrogen introduced with the air, rises into the top of the vessel 211 wherein the effluent gas is combined with lift gas, as hereinafter described, introduced through line 213. The effluent gas is directly contacted in the top of vessel 211 with a spray of quench liquid, in particular aqueous hydrogen chloride, introduced through line 214 to cool the effluent gas and thereby eliminate any vaporized and entrained salts therefrom. The effluent gas, now containing vaporized quench liquid, is withdrawn from vessel 211 through line 215 and introduced into a direct contact quench tower 216, of a type known in the art wherein the effluent gas is cooled by direct contact with a suitable quench liquid, in particular aqueous hydrogen chloride, introduced through line 217 to thereby remove vaporized quench liquid from the effluent gas.

The quench liquid is withdrawn from the bottom of tower 216 through line 218 and a first portion passed through line 214 for quenching the effluent gas in vessel 211. A second portion of the quench liquid is passed through line 219, containing a cooler 221, for introduction into the quench tower 216 through line 217.

An effluent gas, comprised essentially of nitrogen, is withdrawn from quench tower 216 through line 222 and a portion thereof purged through line 223. The remaining portion of the nitrogen effluent gas is compressed in compressor 224 and the temperature thereof regulated in heat exchanger 263 prior to passage through lines 225 and 226 for use as a lift gas for transporting molten salt, as hereinafter described.

The molten salt, now containing copper oxychloride, is withdrawn from the bottom of vessel 211 through line 231 and lifted by the lift gas in line 225 into a separation vessel 232 positioned adjacent the top of the reaction portion of a chlorination vessel 233. In separator 232, the molten salt is separated from the lift gas, with the molten salt being introduced into the top of the reaction portion of chlorination vessel 233 through line 234. The lift gas is withdrawn from vessel 232 through line 235 and combined with lift gas from the oxidation reactor for introduction into the quenching portion of vessel 211 through line 213 to thereby separate any entrained and vaporized salt therefrom.

Fresh feed chlorine and/or hydrogen chloride is introduced into the bottom of reactor 233 through line 241 and fresh feed ethane and/or ethylene, preferably ethane, in line 242 is combined with a recycle chlorinated hydrocarbon stream comprised of ethyl chloride and dichloroethane (1,1- and/or 1,2-dichloroethane) in line 243 and recycled ethane and ethylene in line 244, for introduction into the bottom of vessel 233 through line 245.

The chlorination vessel 233 is operated at the temperatures and pressures hereinabove described to effect chlorination, dehydrogenation and dehydrochlorination of the fresh feed and recycle by direct countercurrent contact of the feed and recycle with the descending molten salt.

An effluent gas, containing vinyl chloride, ethyl chloride, dichloroethane, other chlorinated hydrocarbons, as hereinabove described, ethane, ethylene, water vapor and hydrogen chloride, if any, (the hydrogen chloride produced in the dehydrochlorination reacts with the oxychloride of the salt) rises into the top of vessel 233 wherein the effluent gas is directly contacted with a spray of quench liquid, in particular one or more of the chlorinated hydrocarbons produced in reactor 233, introduced through line 246 to cool the effluent gas and thereby eliminate any vaporized and entrained salts therefrom.

The effluent gas, now containing vaporized quench liquid, is withdrawn from vessel 233 through line 247 and introduced into a separation and recovery section (FIG. 4) for recovery of the various components.

A molten salt is withdrawn from the bottom of reactor 233 through line 261 and lifted by lift gas in line 226 into a separation vessel 262 positioned adjacent the top of reactor 211. In separator 262, the molten salt is separated from the lift gas and introduced through line 210 into vessel 211. The lift gas is withdrawn from separator 262 through line 264 and combined with the lift gas in line 235 for introduction into the top quenching section of vessel 211 through line 213.

Referring now to FIG. 4, the reaction effluent in line 247 is cooled in condenser 310, primarily to condense a portion of the water therefrom (the condensed water would also contain hydrogen chloride, if present) the aforesaid cooling also resulting in the condensation of chlorinated hydrocarbons, including the chlorinated hydrocarbons used as quench liquid. The condensed water and chlorinated hydrocarbons are separated in a separator 311, with a water phase being withdrawn through line 312 and a chlorinated hydrocarbon phase being withdrawn through line 313. A portion of the chlorinated hydrocarbons in line 313 is recycled through line 246 as quench liquid for reactor 233. Alternatively, all of such chlorinated hydrocarbons, if required, may be recycled as quench liquid. The water phase in line 312 is stripped of entrained and dissolved chlorinated hydrocarbon in a stripping column (not shown) and the recovered chlorinated hydrocarbons (from the stripping column) in line 312a are combined with the chlorinated hydrocarbons in line 313. Depending on the amount of hydrogen chloride present in the water, the water may also be treated to recover hydrogen chloride or a concentrated solution of hydrogen chloride.

The remaining portion of the gaseous effluent in line 314 is optionally passed through an alkali scrubbing zone, of a type known in the art, schematically indicated as 315, to remove any remaining hydrogen chloride therefrom.

The gaseous effluent from the alkali scrubbing zone 315, if used, in line 316 is generally passed through a further cooling and separation zone, schematically indicated as 317, to condense further water and chlorinated hydrocarbons therefrom; an acid gas 1,1zone 318, of a type known in the art, to remove any acid gas, primarily carbon dioxide, and a drier 319, and introduced into a fractional distillation column 321. The chlorinated hydrocarbons in line 313 and chlorinated hydrocarbons separated in zone 317 are combined and dried in drier 320 for introduction into column 321. Alternatively, if required, a portion of the chlorinated hydrocarbons recovered in zone 317 may be recycled as quench liquid to reactor 233. The water separated in zone 317 may be passed to a stripping column to recover any chlorinated hydrocarbons with such recovered chlorinated hydrocarbons also being introduced into column 321.

The column 321 is operated at temperatures and pressures to produce a gaseous overhead comprised of ethane and ethylene, which is recovered in line 244 for recycle to reactor 233. A chlorinated hydrocarbon bottoms withdrawn from column 321 through line 322 is introduced into fractional distillation column 323 operated at temperatures and pressures to produce an overhead primarily comprised of vinyl chloride which is recovered through line 324.

A chlorinated hydrocarbon bottoms withdrawn from column 323 through line 325 is introduced into a fractional distillation column 326 operated at temperatures and pressures to recover as overhead dichloroethane (both 1,1 - and 1,2-dichloroethane) and lower boiling chlorinated hydrocarbons, in particular ethyl chloride. The overhead from column 326, comprised essentially of dichloroethane and ethyl chloride is recovered in line 243 for recycle to reactor 233. This overhead may also include minor amounts of dichloroethylenes.

A chlorinated hydrocarbon bottoms from column 326 in line 327 consists primarily of one or more of the following: trichloroethylene, tetrachloroethylene, trichloroethanes and tetrachloroethane.

It should be readily apparent that the overall operation of the embodiment illustrated in FIGs. 3 and 4 is essentially identical to the operation of the embodiment illustrated in FIGS. 1 and 2, except for the elimination of a separate dehydrochlorination reactor and the equipment associated therewith, such as a separate tower for recovering dichloroethane.

The above modifications and numerous other modifications should be apparent to those skilled in the art from the teachings herein.

The following Examples serve to further explain the invention, but it is understood that they are merely illustrative and the invention is not to be regarded as limited thereto. In the following Examples, all parts are by weight, unless otherwise specified.

EXAMPLE I

A molten salt, consisting of 30% potassium chloride and 70% cuprous and cupric chlorides, all by weight, is contacted with air in an oxidation reactor maintained at a temperature of 885°F. The rate of oxygen addition to the molten salt is 330 cm$^3$ per minute.

A molten salt, containing about 2.2 wt. percent of copper oxychloride ($CuO.CuCl_2$), is withdrawn from the oxidation reactor and introduced into a packed chlorination reactor maintained at a temperature of 885°F. The molten salt introduced into the reactor is passed countercurrently to an ethane-chlorine feed, the ethane and chlorine being introduced into the reactor at a rate of flow of 600 cm$^3$/min. and 250 cm$^3$/min., respectively. The overall residence time in the reactor is fifteen seconds.

The effluent withdrawn from the chlorination reactor has the following composition, excluding water and hydrogen chloride:

TABLE I

| Component | Mol. % of $C_2H_6$ Converted |
|---|---|
| $C_2H_4$ | 18.2 |
| $C_2H_3Cl$ | 13.4 |
| $C_2H_5Cl$ | 35.6 |
| $C_2H_2Cl_2$ | 2.0 |
| $C_2H_4Cl_2$ | 23.6 |
| $C_2H_3Cl_3$ | 1.7 |
| $C_2HCl_3$ | 1.2 |
| $C_2Cl_4$ | 0.6 |
| $CO_2$ | 1.7 |
| CO | 1.4 |
| $CH_4$ | 0.6 |
| TOTAL | 100.0 |

The ethane conversion is 59%, with 96.3% of the ethane converted producing chlorinated hydrocarbons and the remainder, carbon oxides and methane. The chlorine introduced into the reactor is converted to chlorinated hydrocarbons at a 75% rate of conversion and the hydrogen chloride produced in situ is converted to chlorine at an 80% rate of conversion.

The 1,2-dichloroethane recovered from the effluent from the chlorination reactor is introduced into a dehydrochlorination reactor at a flow rate of 771 cm$^3$ per minute. The reactor contains the molten salt withdrawn from the chlorination reactor. The molten salt is at a temperature of 849°F. and the total contact time between the molten salt and 1,2-dichloroethane is 4.2 seconds.

The gaseous effluent withdrawn from the dehydrochlorination reactor has the following composition, excluding hydrogen chloride and unconverted 1,2-dichloroethane:

TABLE II

| Component | Mol. % |
|---|---|
| $C_2H_3Cl$ | 99.6 |
| $1,1-C_2H_4Cl_2$ | 0.1 |
| cis $1,2-C_2H_2Cl_2$ | 0.1 |
| $C_2HCl_3$ | 0.05 |
| $C_2Cl_4$ | 0.1 |
| TOTAL | 100.0 |

The conversion of 1,2-dichloroethane is 47%, with a 99.6% selectivity for vinyl chloride.

EXAMPLE II

The procedure of Example I is repeated using the following salt composition in the oxidation reactor, and a temperature of 880°F. and a residence time of 13 seconds in all three reactors:

| KCl | 30 |
|---|---|
| CuCl | 40 |
| $CuCl_2$ | 20 |
| $FeCl_2$ | 10 |
| | 100 |

The effluents from both the chlorination and dehydrochlorination reactors contain vinyl chloride.

EXAMPLE III

The procedure of Example I is repeated using the following salt composition in the oxidation reactor, and a temperature of 920°F. and a residence time of 7 seconds in all three reactors:

| KCl | 34 |
|---|---|
| $FeCl_2$ | 58 |
| $FeCl_3$ | 8 |
| | 100 |

The effluents from both the chlorination and dehydrochlorination reactors contain vinyl chloride.

EXAMPLE IV

The procedure of Example I is repeated using the following salt composition in the oxidation reactor, and a temperature of 890°F. and a residence time of 13 seconds in all three reactors:

| LiCl | 30 |
|---|---|
| CuCl | 50 |
| $CuCl_2$ | 20 |
| | 100 |

The effluents from both the chlorination and dehydrochlorination reactors contain vinyl chloride.

EXAMPLE V

The procedure of Example I is repeated using the following salt composition in the oxidation reactor, and a temperature of 930°F. and a residence time of 6 seconds in all three reactors:

| KCl | 17 |
|---|---|
| $MnCl_2$ | 3 |
| $MnCl_3$ | 80 |
| | 100 |

The effluents from both the chlorination and dehydrochlorination reactors contain vinyl chloride.

EXAMPLE VI

The procedure of Example I is repeated using the following salt composition in the oxidation reactor, and a temperature of 920°F. and a residence time of 7 seconds in all three reactors:

| KCl | 21 |
|---|---|
| $CrCl_2$ | 5 |
| $CrCl_3$ | 74 |
| | 100 |

The effluents from both the chlorination and dehydrochlorination reactors contain vinyl chloride.

EXAMPLE VII

The procedure of Example I is repeated using the following salt composition in the oxidation reactor, and a temperature of 930°F. and a residence time of 6 seconds in all three reactors:

| KCl | 37 |
|---|---|
| $CoCl_2$ | 14 |
| $CoCl_3$ | 49 |
| | 100 |

The effluents from both the chlorination and dehydrochlorination reactors contain vinyl chloride.

EXAMPLE VIII

Ethane and chlorine are introduced into packed bed reactor, flowing upwardly at flow rates of 600 cm³/min. and 250 cm³/min., respectively. Molten salt, consisting of 30 wt. % potassium chloride and 70 wt. % copper chlorides, flows downwardly. The salt could be circulated to and from a sump. Reaction temperature is 885°F. The effluent contains the following:

| Component | Mol. % |
|---|---|
| $C_2H_4$ | 2.1 |
| $C_2H_3Cl$ | 1.6 |
| $C_2H_5Cl$ | 4.3 |
| $C_2H_2Cl_2$ | 0.3 |
| $C_2H_4Cl_2$ | 2.7 |
| $C_2H_3Cl_3$ | 0.3 |
| $C_2HCl_3$ | 0.1 |
| $C_2Cl_4$ | 0.1 |
| $C_2H_6$ | 68.3 |
| HCl | 20.5 |
| | 100.0 |

The ethane conversion is 14.2%. The chlorine is essentially totally converted; 38% to chlorinated hydrocarbons and 62% to hydrogen chloride.

The dichloroethane ($C_2H_4Cl_2$) is contacted separately with the same salt at a temperature of 849°F. The dichloroethane is converted primarily to vinyl chloride and hydrogen chloride via a dehydrochlorination reaction.

EXAMPLE X

This example illustrates the improved results obtained by using a molten salt, as opposed to a supported solid salt, for the dehydrochlorination of dichloroethane.

A. A composition comprising 20 weight percent cupric chloride and 80 weight percent cuprous chloride was placed on a finely divided alumina support (−100 + 200 mesh) and the supported catalyst placed in a fluidized reactor. 1,2-dichloroethane was passed through the fluidized supported catalyst at a temperature of 880°F. and a residence time of 11 seconds.

The conversion of 1,2-dichloroethane was 42.4%; and the selectivity to vinyl chloride was 87.6%.

B. A composition comprising 20 weight percent cupric chloride and 80 weight percent cuprous chloride was combined with potassium chloride to provide a composition which contains 30 weight percent potassium chloride and the composition was placed on a finely divided alumina support (−100 + 200 mesh). The supported catalyst was placed in a fluidized reactor. 1,2-dichloroethane was passed through the fluidized supported catalyst at a temperature of 880°F. and a residence time of 11.5 seconds.

The conversion of 1,2-dichloroethane was 49.6%; and the selectivity to vinyl chloride was 83.8%.

C. A composition comprising 20 weight percent cupric chloride and 80 weight percent cuprous chloride was formed into a melt by the addition of potassium chloride, the potassium chloride being 30 weight percent of the melt. 1,2-dichloroethane was circulated through a reactor in contact with the melt at a temperature of 881°F. and a residence time of 10 seconds.

The conversion of 1,2-dichloroethane was 92.4% and the selectivity to vinyl chloride was 97.8%.

The hereinabove example illustrates that dehydrochlorination as effected in the present invention results in high vinyl chloride selectivity in combination with high rates of conversion.

EXAMPLE XI

The following Table is illustrative of operating conditions which may be employed in the embodiment of FIGS. 1 and 2 to produce vinyl chloride at the rate of 155 million pounds per year. The molten salt is introduced into reactor 15 at a temperature of 850°F. and withdrawn at a temperature of 840°F. The molten salt is introduced into reactor 35 at a temperature of 840°F. and withdrawn at a temperature of 825°F. The symbol Σ indicates that the stated quantity represents the total amount including various isomers of the component.

TABLE

| LINE | 12 | 10 | 13 | 28 | 31/93 | 32/83 | 33 | 34 | 45 | 46/95 | 57 | 86 | 94+96 |
|---|---|---|---|---|---|---|---|---|---|---|---|---|---|
| TEMP. °F. | 300° | 825° | 850° | 100° | 100° | 100° | 100° | 100° | 230° | 300° | 250° | 100° | 100° |
| TOTAL LBS./HR. | 43,222 | 7,423,705 | 7,432,185 | 34,742 | 11,539 | 21,188 | 14,342 | 10,080 | 65,759 | 18,881 | 18,848 | 18,756 | 4,434 |
| COMPONENT (LB. MOL/HR.) | | | | | | | | | | | | | |
| $O_2$ | 312 | | | 47 | | | | | | | | | |
| $N_2$ | 1,180 | | | 1,180 | | | | | | | | | |
| CO | | | | | | | 2 | | | 2 | | | |
| $CO_2$ | | | | | | | | | | 8 | | | |
| $Cl_2$ | | | | | | | | 202 | | | | | |
| HCl | | | | | 162 | | | | | 6 | | 162 | |
| $H_2O$ | 11 | | | 11 | | | | | | 514 | | | |
| $C_2H_4$ | | | | | 206 | | | | | 206 | | | |
| $C_2H_6$ | | | | | | 311 | | | 336 | 311 | | | |
| $C_2H_3Cl$ | | | | 3 | 2 | | | | | 142 | | 162 | 300 |
| $C_2H_5Cl$ | | | | 142 | | | | | | 142 | | | 0.1 |
| $\Sigma C_2H_2Cl_2$ | | | | 8 | | | | | | 20 | 8 | 9 | 3 |
| $\Sigma C_2H_4Cl_2$ | | | | 15 | | | | | | 181 | 176 | 13 | 3 |
| $\Sigma C_2H_3Cl_3$ | | | | | | | | | | 10 | 1 | 1 | 11 |
| $C_2HCl_3$ | | | | | | | | | | 1 | 4 | 4 | 1 |
| $C_3H_6Cl_2$ | | | | | | | | | | 1 | | | 1 |
| $C_2Cl_4$ | | | | | | | | | | 7 | | | 7 |
| $CCl_4$ | | | | | | | | | | 1 | 1 | | |
| CuO | | | 530 | | | | | | | | | | |
| CuCl | | 41,960 | 40,900 | | | | | | | | | | |
| $CuCl_2$ | | 11,570 | 12,100 | | | | | | | | | | |
| KCl | | 23,000 | 23,000 | | | | | | | | | | |

The process of the present invention provides an effective method of producing vinyl chloride from either ethane and/or ethylene. In particular, the production of vinyl chloride in accordance with the present invention is advantageous as a result of the ability to replace the ethylene feedstock, conventionally employed in the art, with an ethane feedstock.

In accordance with the present invention, unreacted feed and intermediate reaction products are effectively converted to vinyl chloride product without significant loss of chlorine values, thereby providing an economic process.

Still another distinct advantage of the present invention, is that dichloroethane may be dehydrochlorinated in the presence of the hereinabove described melts to vinyl chloride at conversion rates higher than those generally employed in the art while retaining high vinyl chloride selectivity. Thus, in accordance with the present invention, it is possible to convert 1,2-dichloroethane, the primary or in some cases the only component of the dichloroethane intermediate, at a rate of 90% or better while providing vinyl chloride selectivity in the order of 90% or better, unlike prior processes in which 1,2-dichloroethane could not be converted at such high rates while retaining high vinyl chloride selectivity.

Numerous modifications and variations of the invention are possible within the above teachings and therefore the invention may be practised otherwise than as particularly described.

What is claimed is:

1. A process for producing vinyl chloride, comprising:
   a. contacting at a temperature of from about 700°F to about 1200°F a feed comprising a member selected from the group consisting of ethane, ethylene and mixtures thereof with a melt comprising a multivalent metal chloride in both its higher and lower valence state to produce a reaction effluent comprising vinyl chloride and 1,2-dichloroethane, said multivalent metal chloride being selected from the group consisting of the chlorides of copper, chromium, cobalt, manganese and iron;
   b. recovering 1,2-dichloroethane and vinyl chloride from the reaction effluent;
   c. dehydrochlorinating at a temperature of from about 700°F to about 1200°F recovered 1,2-dichloroethane to vinyl chloride by contacting the 1,2-dichloroethane with a melt comprising a multivalent metal chloride in both its higher and lower valence state in an amount effective to catalyze the dehydrochlorination of 1,2-dichloroethane to vinyl chloride, said multivalent metal chloride being selected from the group consisting of the chlorides of copper, chromium, cobalt, manganese and iron.

2. The process as defined in claim 1 wherein the multivalent metal chloride used in steps (a) and (c) is copper chloride.

3. The process as defined in claim 2 wherein the hydrocarbon employed in step (a) is ethane.

4. The process as defined in claim 2 wherein the melt in step (a) further includes copper oxychloride.

5. The process as defined in claim 4 wherein the feed in step (a) further includes a member selected from the group consisting of chlorine, hydrogen chloride and mixtures thereof.

6. The process as defined in claim 5 wherein the melt further includes as a melting point depressant a member selected from the group consisting of alkali metal chlorides and the heavy metal chlorides of Groups I, II, III and IV of the Periodic Table.

7. The process as defined in claim 6 wherein the melting point depressant is an alkali metal chloride.

8. A process for producing vinyl chloride, comprising:
   a. contacting a melt comprising a multivalent metal chloride in both its higher and lower valence state with a molecular oxygen-containing gas to produce the oxychloride of the metal, said multivalent metal chloride being selected from the group consisting of the chlorides of copper, chromium, cobalt, manganese and iron;
   b. contacting at a temperature of from about 700°F to about 1200°F melt obtained from step (a) with a hydrocarbon selected from the group consisting of ethane, ethylene and mixtures thereof and a member selected from the group consisting of chlorine, hydrogen chloride and mixtures thereof to produce a reaction effluent comprising vinyl chloride and 1,2-dichloroethane;
   c. recovering vinyl chloride and 1,2-dichloroethane from the reaction effluent; and
   d. dehydrochlorinating recovered 1,2-dichloroethane to vinyl chloride by contacting at a temperature of from about 700°F to about 1200°F recovered 1,2-dichloroethane with a melt comprising a multivalent metal chloride in both its higher and lower valence state in an amount effective to catalyze the dehydrochlorination of 1,2-dichloroethane to vinyl chloride, said multivalent metal chloride being selected from the group consisting of the chlorides of copper, chromium, cobalt, manganese and iron.

9. The process of claim 8 wherein the contacting of step (a) is effected at a temperature from about 600°F to about 900°F.

10. The process as defined in claim 8 wherein the multivalent metal used in steps (a), (b) and (d) is copper.

11. The process as defined in claim 10 wherein the hydrocarbon of step (b) is ethane.

12. The process as defined in claim 10 wherein the melt further includes a metal chloride melting point depressant which is non-volatile and resistant to the action of oxygen to maintain the molten state at the reaction temperature.

13. The process as defined in claim 12 wherein the melting point depressant is selected from the group consisting of the chlorides of alkali metals, zinc, silver and thallium.

14. The process as defined in claim 12 wherein the melting point depressant is an alkali metal chloride.

15. The process as defined in claim 14 wherein the alkali metal chloride is potassium chloride.

16. The process as defined in claim 12 wherein the reaction effluent of step (b) also includes ethane, ethylene, and ethyl chloride, said ethane, ethylene, and ethyl chloride being recovered from the reaction effluent and recycled to step (b).

17. The process as defined in claim 10 wherein steps (b) and (d) are effected in separate reaction zones and the melt employed in step (d) is obtained from step (b).

18. The process as defined in claim 17 wherein the reaction effluent from step (b) also includes 1,1-dichloroethane, said 1,1-dichloroethane being recovered and passed to step (d) for dehydrochlorination to vinyl chloride.

19. The process as defined in claim 17 wherein the reaction effluent from step (b) also includes 1,1-dichloroethane, said 1,1-dichloroethane being recovered and passed to step (b) for dehydrochlorination to vinyl chloride.

20. The process as defined in claim 10 wherein steps (b) and (d) are effected in separate reaction zones and at least a portion of the melt employed in step (d) is obtained from step (a).

21. The process as defined in claim 20 wherein the melt includes as a melting point depressant to maintain the molten state at the reaction temperature an alkali metal chloride.

22. The process as defined in claim 21 wherein the reaction effluent from step (b) further includes, ethane, ethylene and ethyl chloride which are recovered and recycled to step (d).

23. A process for producing vinyl chloride, comprising:
   a. contacting in a first reaction zone a vapor feed comprising, ethane and a member selected from the group consisting of chlorine, hydrogen chloride and mixtures thereof, with a molten mixture comprising cuprous chloride, cupric chloride, copper oxychloride and potassium chloride, said contacting being effected at a temperature from about 700°F to about 1200°F;
   b. withdrawing a first gaseous effluent from the first reaction zone comprising vinyl chloride and 1,2-dichloroethane;

c. recovering vinyl chloride from the first gaseous effluent as reaction product;

d. recovering 1,2-dichloroethane from the first gaseous effluent and introducing recovered gaseous 1,2-dichloroethane into a second reaction zone wherein the 1,2-dichloroethane is contacted with a molten mixture comprising cupric chloride, cuprous chloride and potassium chloride in an amount effective to catalyze the dehydrochlorination of 1,2-dichloroethane to vinyl chloride, said contacting being effected at a temperature from about 700°F to about 1200°F to dehydrochlorinate 1,2-dichloroethane to vinyl chloride;

e. withdrawing a second gaseous effluent, comprising vinyl chloride, from the second reaction zone and recovering therefrom as reaction product vinyl chloride;

f. contacting in a third reaction zone at a temperature from about 600°F to about 900°F melt recovered from step (d) with gaseous molecular oxygen to produce copper oxychloride; and g. passing melt recovered from step (f) to step (a).

24. The process as defined in claim 23 wherein the molten mixture employed in step (d) is obtained from step (a).

25. The process as defined in claim 23 wherein the molten mixture employed in step (a) contains from about 20 to about 40 weight percent potassium chloride with the remainder being copper chlorides and oxychloride.

26. The process as defined in claim 25 wherein the first gaseous effluent further includes 1,1-dichloroethane, said 1,1-dichloroethane being recovered and passed to step (d) for dehydrochlorination to vinyl chloride.

27. The process as defined in claim 25 wherein the first gaseous effluent further includes 1,1-dichloroethane, said 1,1-dichloroethane being recovered and passed to step (a) for dehydrochlorination to vinyl chloride.

28. The process as defined in claim 25 wherein the second gaseous effluent includes hydrogen chloride which is recovered and recycled to step (a).

29. The process as defined in claim 25 wherein the molten mixture employed in step (d) is obtained from step (f) whereby the molten mixture in step (d) further includes copper oxychloride and the molten mixture recovered from step (a) is also passed to step (f).

30. The process as defined in claim 29 wherein the first gaseous effluent further includes ethane, ethylene and ethyl chloride which is recovered and passed to step (d).

31. A continuous process for producing vinyl chloride, comprising:

a. contacting in a first reaction zone a vapor feed comprising, as fresh feed, ethane and a member selected from the group consisting of chlorine, hydrogen chloride and mixtures thereof and as recycle, unconverted ethane, ethylene and ethyl chloride, with a molten mixture comprising cuprous chloride, cupric chloride, copper oxychloride and potassium chloride, said contacting being effected at a temperature from about 700°F to about 1200°F;

b. withdrawing a first gaseous effluent from the first reaction zone comprising ethane, ethylene, vinyl chloride, 1,2-dichloroethane and ethyl chloride;

c. recovering from the first gaseous effluent and recycling to the first reaction zone ethane, ethylene, and ethyl chloride;

d. recovering vinyl chloride from the first gaseous effluent as reaction product;

e. recovering 1,2-dichloroethane from the first gaseous effluent and introducing recovered gaseous 1,2-dichloroethane into a second reaction zone wherein the 1,2-dichloroethane is contacted with a molten mixture comprising cupric chloride, cuprous chloride and potassium chloride, in an amount effective to catalyze the dehydrochlorination of 1,2-dichloroethane to vinyl chloride, said contacting being effected at a temperature from about 700°F to about 1200°F to dehydrochlorinate 1,2-dichloroethane to vinyl chloride;

f. withdrawing from the second reaction zone a second gaseous effluent, comprising vinyl chloride and recovering therefrom as reaction product vinyl chloride;

g. contacting in a third reaction zone at a temperature from about 600°F to about 900°F melt recovered from step (e) with gaseous molecular oxygen to produce copper oxychloride; and h. passing melt recovered from step (g) to step (a).

32. The process as defined in claim 31 wherein the molten mixture employed in step (e) is obtained from step (a) and the second gaseous effluent further comprises hydrogen chloride and further comprising: recovering hydrogen chloride from the second gaseous effluent; and recycling the hydrogen chloride recovered from the second gaseous effluent to step (a).

33. The process as defined in claim 32 wherein the molten mixture employed in step (a) contains from about 20 to about 40 weight percent potassium chloride with the remainder being copper chlorides and oxychloride.

34. The process as defined in claim 33 wherein the contacting of steps (a), (e) and (g) is effected countercurrently.

35. The process as defined in claim 31 wherein the first gaseous effluent also comprises 1,1-dichloroethane, said 1,1-dichloroethane being recovered and passed to step (a) for dehydrochlorination to vinyl chloride.

36. The process as defined in claim 31 wherein the first gaseous effluent also comprises 1,1-dichloroethane, said 1,1-dichloroethane being recovered and passed to step (d) for dehydrochlorination to vinyl chloride.

37. The process as defined in claim 31 wherein the molten mixture employed in step (e) is obtained from step (g), whereby the molten mixture in step (e) further includes copper oxychloride, and the molten mixture recovered from step (a) is also passed to step (g).

38. A process for producing vinyl chloride, comprising:

a. contacting in a first reaction zone a vapor feed comprising ethane, a member selected from the group consisting of chlorine, hydrogen chloride and mixtures thereof and recycle 1,2-dichloroethane with a molten mixture comprising cuprous chloride, cupric chloride, copper oxychloride and potassium chloride, in an amount effective to catalyze the dehydrochlorination of 1,2-dichloroethane to vinyl chloride, said contacting being effected at a temperature from about 700°F to about 1200°F;

b. withdrawing a gaseous effluent from the first reaction zone comprising vinyl chloride and 1,2-dichloroethane;
c. recovering vinyl chloride from the gaseous effluent as reaction product;
d. recovering 1,2-dichloroethane from the gaseous effluent and recycling 1,2-dichloroethane to the first reaction zone;
e. recovering the molten mixture from step (a) and contacting recovered molten mixture in a second reaction zone with gaseous molecular oxygen to produce copper oxychloride said contacting being effected at a temperature from 600°F to about 900°F; and
f. recovering molten mixture from step (e) and passing recovered molten mixture from step (e) to step (a).

39. The process as defined in claim 38 wherein the molten mixture employed in step (a) contains from about 20 to about 40 weight percent potassium chloride with the remainder being copper chlorides and oxychloride.

40. A continuous process for producing vinyl chloride, comprising:
a. contacting in a first reaction zone a vapor feed comprising, as fresh feed, ethane and a member selected from the group consisting of chlorine, hydrogen chloride and mixtures thereof and as recycle, unconverted ethane, ethylene, 1,2-dichloroethane and ethyl chloride, with a molten mixture comprising cuprous chloride, cupric chloride, copper oxychloride and potassium chloride, in an amount effective to catalyze the dehydrochlorination of 1,2-dichloroethane to vinyl chloride, said contacting being effected at a temperature from about 700°F to about 1200°F;
b. withdrawing a gaseous effluent from the first reaction zone comprising ethane, ethylene, vinyl chloride, 1,2-dichloroethane and ethyl chloride;
c. recovering from the first gaseous effluent and recycling to the first reaction zone ethane, ethylene, 1,2-dichloroethane and ethyl chloride;
d. recovering vinyl chloride from the gaseous effluent as reaction product;
e. contacting in a second reaction zone at a temperature from about 600°F to about 900°F melt recovered from step (a) with gaseous molecular oxygen to produce copper oxychloride; and
f. passing melt recovered from step (e) to step (a).

41. The process as defined in claim 40 wherein the molten mixture employed in step (a) contains from about 20 to about 40 weight percent potassium chloride with the remainder being copper chlorides and oxychloride.

42. The process as defined in claim 41 wherein the contacting of steps (a) and (e) is effected countercurrently.

43. The process as defined in claim 40 wherein the gaseous effluent also comprises 1,1-dichloroethane, said 1,1-dichloroethane being recovered and passed to step (a) for dehydrochlorination to vinyl chloride.

* * * * *

UNITED STATES PATENT OFFICE
CERTIFICATE OF CORRECTION

Patent No. 3,937,744      Dated February 10, 1976

Inventor(s) Herbert Riegel

It is certified that error appears in the above-identified patent and that said Letters Patent are hereby corrected as shown below:

Column 3, line 45, "dischloroethane" should read -- dichloroethane --.

Column 12, line 41, "concurrently" should be -- cocurrently --.

Column 14, line 48, "this" should be -- thus --.

Column 17, line 41, "1,1" should be -- removal --.

Column 21, line 61, "witth" should be -- with --.

Signed and Sealed this

Twelfth Day of October 1976

[SEAL]

Attest:

RUTH C. MASON
*Attesting Officer*

C. MARSHALL DANN
*Commissioner of Patents and Trademarks*